United States Patent [19]

Soslau

[11] 4,344,936
[45] Aug. 17, 1982

[54] PLATELET COMPOSITION HAVING IMPROVED STORAGE STABILITY AND METHOD THEREFOR

[76] Inventor: Gerald Soslau, 509 Grandview Ave., Feasterville, Pa. 19047

[21] Appl. No.: 188,121

[22] Filed: Sep. 17, 1980

[51] Int. Cl.$^3$ .............................................. A61K 35/44
[52] U.S. Cl. ...................................... 424/101; 435/2
[58] Field of Search ............................ 424/101; 435/2

[56] References Cited

PUBLICATIONS

Kovacs et al.–Chem. Abst. vol. 92 (1980) p. 104,180z.
Davis et al.–Chem. Abst. vol. 78 (1973) p. 92,819k.

*Primary Examiner*—Sam Rosen
*Attorney, Agent, or Firm*—Paul T. Meiklejohn

[57] ABSTRACT

There is disclosed, in one aspect, a composition for improving the storage stability of blood platelets comprising the platelets, a container for the platelets, and a sialyl compound having the structural formula (I)

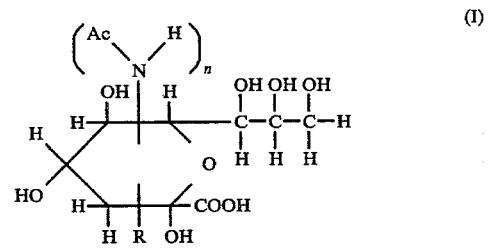

wherein Ac is an acetyl group, R is a carbohydrate group, n is an integer of 1 or more, preferably 1, and the R and N-acetyl groups replace hydrogen atoms or hydroxyl groups on the ring. In another aspect, there is disclosed a method for increasing the storage stability of these platelets. This method comprises admixing with the platelets a compound having the structural formula (I) described above, wherein Ac, R, and n have the meanings described above.

9 Claims, No Drawings

PLATELET COMPOSITION HAVING IMPROVED STORAGE STABILITY AND METHOD THEREFOR

BACKGROUND OF THE INVENTION

This invention relates generally to improvements in the storage stability of blood platelets or thrombocytes. More particularly, this invention relates to a platelet composition having improved storage stability by the addition of particular chemical compounds.

Whole blood contains various components such as red blood cells, white blood cells, blood platelets, and plasma (which include both glycoproteins and serum). These various components may be separated by centrifugation means which are well known to those skilled in this art. For example, when whole blood is subjected to centrifugal forces, the plasma and platelets, being the lighter fraction, accumulate at the top of the centrifuge container and may be removed from the other components of the whole blood. If this plasma/platelet fraction is subsequently subjected to further centrifugal force, the platelets tend to the bottom and the plasma to the top of the centrifuge container. The platelet-rich lower fraction may then be removed, re-suspended in a small amount of plasma, and stored as such for subsequent transfusion. A 500-milliliter unit of whole blood produces from 40 to 50 milliliters of this platelet concentrate suspended in plasma. The plasma concentrate is stored in plastic bags on a rotating platform to inhibit the settling out of the platelets.

Blood platelets are produced in the bone marrow. They circulate in the bloodstream and are essential in normal clot formation.

Certain classes of persons, such as leukemics, experience platelet insufficiency, a condition known as thrombocytopenia. Such persons, on occasion, require an infusion of platelets.

Platelet concentrates obtained from healthy blood donors have a shelf-life of about three days, after which time they are of no clinical value because, when transfused, they are rapidly removed from the circulation. Thousands upon thousands of platelet concentrates become outdated before they can be used clinically because of the relatively short storage lifetime of platelet concentrates.

Platelets have a life span in the bloodstream of about seven to ten days. They are removed from circulation by becoming attached to a cell in the liver or spleen. The platelet is pulled into the cell and broken down into various components. The mechanism which some believe to account for this process is the removal of sialic acid residues from the platelets. In this connection, see "Effects on Platelet Function of Removal of Platelet Sialic Acid by Neuraminidase", 32 *Lab. Invest.* 476 (1975) (Greenberg et al.).

The search has continued concerning the problem of platelet lifetime in storage. This invention was made as a result of that search.

OBJECTS AND SUMMARY OF THE INVENTION

Accordingly, it is a general object of the present invention to avoid or substantially alleviate the above problems.

A more specific object of the present invention is to provide a composition for improving the storage stability of blood platelets.

Another object of the present invention is to provide a method for increasing the storage stability of blood platelets.

Other objects and advantages of the present invention will become apparent from the following summary of the invention and description of its preferred embodiments.

In one aspect, the present invention provides a composition for improving the storage stability of blood platelets. This composition comprises the platelets, a container for the platelets, and a sialyl compound having the structural formula (I)

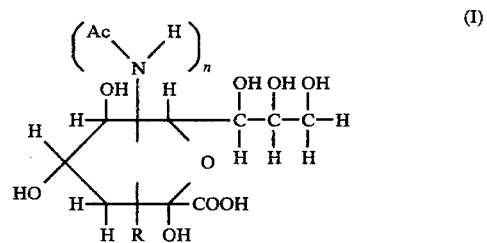

wherein Ac is an acetyl group, R is a carbohydrate group, n is an integer of 1 or more, preferably 1, and the R and N-acetyl groups replace hydrogen atoms or hydroxyl groups on the ring.

In another aspect, the present invention provides a method for increasing the storage stability of blood platelets. This method comprises admixing with the platelets the compound of structural formula (I) as described above.

DESCRIPTION OF THE PREFERRED EMBODIMENTS

Sialic acid has the structural formula (II)

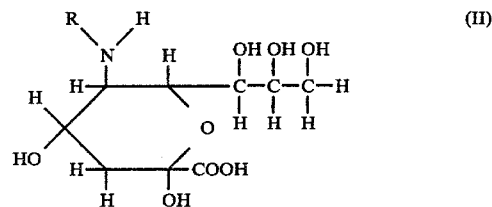

wherein Ac represents an acetyl group and n is an integer of 1 or more, preferably 1, and the N-acetyl groups replace preferably hydroxyl groups on the ring, preferably the hydroxyl group at the 5-position.

N-acetyl neuraminyl lactose, which is derived from bovine mammary glands, and which is commercially available from the Sigma Chemical Co. of St. Louis, Mo. is a neuraminic acid derivative having the structural formula III

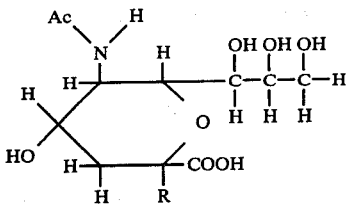

(III)

wherein Ac and n have the meanings given above and R represents lactose. The R group preferably replaces an hydroxyl on the ring and preferably at the 2-position.

The term "sialyl-compound" is meant to describe the compounds within the scope of Formula I as set forth above.

A preferred R group is lactose although any other carbohydrate such as galactose may also be used. Both mono and polysaccharides may be used as the R group. Mixtures of different sialyl compounds, with different R groups on each, may also be used. A particularly preferred sialyl compound is N-acetyl neuraminyl lactose which is 0-(N-acetyl-neuraminyl) (2→3)0-β-D-galactopyranosyl-(1→4)-D-glucopyranose.

The sialyl compound should be contained in the plastic bag into which the platelet concentrate is added after it is separated from the other whole blood fractions. As noted hereinabove, the typical platelet concentrate is stored in plastic bags which hold approximately fifty milliliters of platelet concentrate suspended in plasma.

The amount of sialyl compound which may be added varies widely, although generally less than about 0.04, typically at least about 0.01, and preferably from about 0.025 to about 0.03% by weight based upon 100 milliliters of the platelet concentrate may be used. Amounts of sialyl compound in excess of 0.04% by weight may, of course, be employed but it is not believed that any additional advantage as to storage stability is obtained from these amounts vis-a-vis the use of 0.04% by weight sialyl compound. Furthermore, amounts of sialyl compound less than about 0.01% by weight may have some affect on storage stability, but it is believed that at least 0.01% by weight sialyl compound is needed to note a practical advantage in storage stability.

The above recited percentages are in terms of N-acetyl neuraminyl lactose. The amount of sialyl compound which is used will change slightly depending upon the particular number and kind of R and N-acetyl groups on the molecule because of small changes in the molecular weight of the molecule due to these differences.

It has been found that when 0.028% by weight of sialyl compound (based upon 100 milliliters of platelet concentrate) is added to the platelet concentrate, the platelets may be stored for at least seven days without deleterious breakdown, a storage increase of more than 50% over that of platelet concentrate absent of the addition of sialyl compound.

The platelets containing the sialyl compound are stored in plastic bags as described above. These plastic bags are well known to those skilled in this art and are commercially available under the trademark FENWAL from the Travenol Co., of Illinois. The bags are stored at room temperature on a rotating platform so as to inhibit the settling out of the platelets.

Improved storage stability also results when the sialyl compound of the present invention is added to sialic acid containing glycoproteins which are derived from plasma.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

I claim:

1. A composition for improving the storage stability of blood platelets comprising (a) said platelets, (b) a container for said platelets, and (c) an effective amount of a sialyl compound having the structural formula (I)

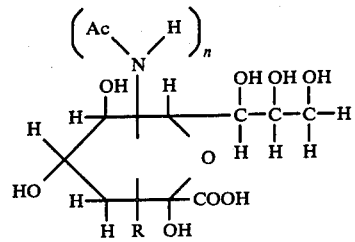

wherein Ac is an acetyl group, R is a carbohydrate group, n is an integer of 1 or more, and the R group replaces an hydroxyl group on the ring and the N-acetyl group replaces hydroxyl groups.

2. The composition of claim 1, wherein the amount of sialyl compound is less than 0.04% by weight based upon the volume of 100 milliliters of platelet concentrate.

3. The composition of claim 1, wherein said sialyl compound has the structural formula (III)

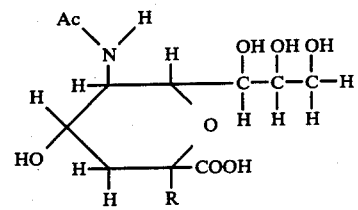

wherein R is a carbohydrate.

4. The composition of claim 3, wherein R is a member selected from the group consisting of lactose and galactose.

5. The composition of claim 1, wherein said container is a plastic bag.

6. A method for increasing the storage stability of blood platelets comprising admixing with said platelets an effective amount of a sialyl compound having the structural formula (I)

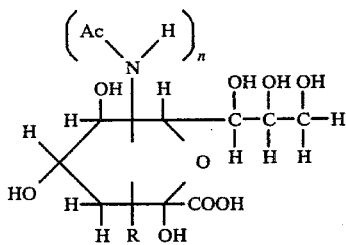

wherein Ac is an acetyl group, R is a carbohydrate group, n is an integer of 1 or more, and the R group replaces an hydroxyl group on the ring and the N-acetyl group replaces hydroxyl groups.

7. The method of claim 6, wherein the amount of sialyl compound is less than about 0.04% by weight based upon the volume of 100 milliliters of platelet concentrate.

8. The method of claim 6, wherein said sialyl compound has the structural formula (III)

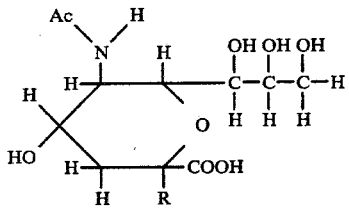

wherein R is a carbohydrate.

9. The method of claim 8, wherein R is a member selected from the group consisting of lactose and galactose.

* * * * *